United States Patent
Ortiz et al.

(10) Patent No.: US 7,763,039 B2
(45) Date of Patent: Jul. 27, 2010

(54) ARTICULATING BLUNT DISSECTOR/GASTRIC BAND APPLICATION DEVICE

(75) Inventors: Mark S. Ortiz, Milford, OH (US); David N. Plescia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 722 days.

(21) Appl. No.: 11/449,875

(22) Filed: Jun. 9, 2006

(65) Prior Publication Data

US 2007/0288048 A1    Dec. 13, 2007

(51) Int. Cl.
*A61B 17/04* (2006.01)
(52) U.S. Cl. .................................................... 606/148
(58) Field of Classification Search ............... 600/37; 606/139, 142, 144, 145, 148, 153, 113
See application file for complete search history.

(56) References Cited

U.S. PATENT DOCUMENTS

| | | | |
|---|---|---|---|
| 4,134,405 A | 1/1979 | Smit | |
| 4,592,339 A | 6/1986 | Kuzmak et al. | |
| 4,696,288 A | 9/1987 | Kuzmak et al. | |
| 4,760,837 A | 8/1988 | Petit | |
| 4,935,027 A * | 6/1990 | Yoon | 606/146 |
| 5,033,481 A | 7/1991 | Heyler, III | |
| 5,065,772 A | 11/1991 | Cox, Jr. | |
| 5,074,868 A | 12/1991 | Kuzmak | |
| 5,083,576 A | 1/1992 | Ruiz-Razura et al. | |
| 5,160,338 A | 11/1992 | Vincent | |
| 5,226,429 A | 7/1993 | Kuzmak | |
| 5,601,604 A | 2/1997 | Vincent | |
| 5,658,298 A | 8/1997 | Vincent et al. | |
| RE36,176 E | 3/1999 | Kumzak | |
| 5,910,149 A | 6/1999 | Kuzmak | |
| 6,067,991 A | 5/2000 | Forsell | |
| 6,102,922 A | 8/2000 | Jakobsson et al. | |
| 6,171,316 B1 * | 1/2001 | Kovac et al. | 606/144 |
| 6,210,347 B1 | 4/2001 | Forsell | |
| 6,450,173 B1 | 9/2002 | Forsell | |
| 6,450,946 B1 | 9/2002 | Forsell | |
| 6,453,907 B1 | 9/2002 | Forsell | |

(Continued)

FOREIGN PATENT DOCUMENTS

EP    1319371    6/2006

(Continued)

OTHER PUBLICATIONS

Agency for Medical Innovations, Ltd. Soft Gastric Band Premium Implant, Product Information Sheet.

*Primary Examiner*—(Jackie) Tab-Uyen T. Ho
*Assistant Examiner*—Son Dang
(74) *Attorney, Agent, or Firm*—Welsh & Flaxman LLC

(57) ABSTRACT

A single handed articulating blunt dissector/gastric band application device includes a support shaft connecting a handle at a first end of the device to an articulating assembly at a second end of the device. The handle includes an actuation mechanism linked to the articulating assembly for controlling movement thereof. The second end includes a proximal end and a distal end, wherein the distal end includes a blunt distal tip shaped and dimensioned for dissecting tissue without unduly causing trauma to the tissue. The second end also includes a suture grasping notch shaped and dimensioned for engaging and pulling a gastric band.

10 Claims, 3 Drawing Sheets

U.S. PATENT DOCUMENTS

| | | |
|---|---|---|
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Fosell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,511,490 B2 | 1/2003 | Robert |
| 6,547,801 B1 | 4/2003 | Dargent et al. |
| 6,676,674 B1 | 1/2004 | Dudai |
| 6,709,385 B2 | 3/2004 | Forsell |
| 6,915,165 B2 | 7/2005 | Forsell |
| 6,916,326 B2 | 7/2005 | Benchetrit |
| 6,953,429 B2 | 10/2005 | Forsell |
| 6,966,875 B1 | 11/2005 | Longobardi |
| 7,011,624 B2 | 3/2006 | Forsell |
| 2003/0105385 A1 | 6/2003 | Forsell |
| 2003/0114729 A1 | 6/2003 | Forsell |
| 2004/0049209 A1 | 3/2004 | Benchetrit |
| 2004/0158272 A1 | 8/2004 | Hofle et al. |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2005/0002984 A1 | 1/2005 | Byrum et al. |
| 2005/0038458 A1 | 2/2005 | Bailly et al. |
| 2005/0070937 A1 | 3/2005 | Jambor et al. |
| 2005/0119672 A1 | 6/2005 | Benchetrit |
| 2005/0131391 A1 | 6/2005 | Chu |
| 2005/0183730 A1 | 8/2005 | Byrum |
| 2005/0187566 A1 | 8/2005 | Byrum et al. |
| 2005/0277963 A1 | 12/2005 | Fields |
| 2006/0074439 A1 | 4/2006 | Garner et al. |
| 2007/0179510 A1* | 8/2007 | Stone .................. 606/148 |
| 2007/0185518 A1* | 8/2007 | Hassler, Jr. .................. 606/190 |
| 2008/0177281 A1* | 7/2008 | Weitzner et al. ............ 606/130 |

FOREIGN PATENT DOCUMENTS

| | | |
|---|---|---|
| EP | 1815801 | 8/2007 |
| EP | 1829506 | 9/2007 |
| WO | WO2004/108025 | 12/2004 |
| WO | WO2005/072195 | 8/2005 |
| WO | WO2005/072664 | 8/2005 |

\* cited by examiner

ARTICULATING BLUNT DISSECTOR/GASTRIC BAND APPLICATION DEVICE

BACKGROUND OF THE INVENTION

1. Field of the Invention

The invention relates to a gastric band application device. More particularly, the invention relates to an articulating blunt dissector/gastric band application device.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. Other forms of bariatric surgery include Fobi pouch, bilio-pancreatic diversion, and gastroplastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is a type of gastric reduction surgery attempting to limit food intake by reducing the size of the stomach. In contrast to RYGB and other stomach reduction procedures, gastric-banding does not require the alteration of the anatomy of the digestive tract in the duodenum or jejunum.

Since the early 1980s, gastric bands have provided an effective alternative to gastric bypass and other irreversible surgical weight loss treatments for the morbidly obese. Several alternative procedures are performed under the heading of gastric-banding. Some banding techniques employ a gastric ring, others use a band, some use stomach staples and still other procedures use a combination of rings, bands and staples. Among the procedures most commonly performed are lap band, vertical banded gastroplasty (VBG), silastic ring gastroplasty (SRG), and adjustable silastic gastric banding (AGB).

In general, the gastric band is wrapped around an upper portion of the patient's stomach, forming a stoma that is less than the normal interior diameter of the stomach. This restricts food passing from an upper portion to a lower digestive portion of the stomach. When the stoma is of an appropriate size, food held in the upper portion of the stomach provides a feeling of fullness that discourages overeating.

Typically, the gastric band is laparoscopically introduced into a patient's abdomen by pushing it through a trocar. A variety of delivery devices have been developed for this purpose. However, currently available delivery devices exhibit many shortcomings, including, but not limited to the fact that they are difficult to sterilize, require two hands for proper operation thereof and exhibit weakness when moved in key directions. As such, a need currently exists for improved gastric band delivery systems providing for convenient and reliable delivery of gastric bands. The present invention provides such a gastric band delivery technique.

SUMMARY OF THE INVENTION

It is, therefore, an object of the present invention to provide a single handed articulating blunt dissector/gastric band application device. The device includes a support shaft connecting a handle at a first end of the device to an articulating assembly at a second end of the device. The handle includes an actuation mechanism linked to the articulating assembly for controlling movement thereof. The second end includes a proximal end and a distal end, wherein the distal end includes a blunt distal tip shaped and dimensioned for dissecting tissue without unduly causing trauma to the tissue. The second end also includes a suture grasping notch shaped and dimensioned for engaging and pulling a gastric band.

It is also an object of the present invention to provide a device wherein the suture grasping notch is obliquely oriented relative to a longitudinal axis of the device.

It is another object of the present invention to provide a device wherein the suture grasping notch is oriented at a 45 degree angle relative to the longitudinal axis of the device.

It is a further object of the present invention to provide a device wherein the articulating assembly is proximally oriented relative to the suture grasping notch.

It is also another object of the present invention to provide a device wherein the articulating assembly includes a flex member composed of a first side member and a second side member.

It is yet another object of the present invention to provide a device wherein the first side member and the second side member are substantially parallel and are spaced from each other as they extend along the second end of the device.

It is also an object of the present invention to provide a device wherein the first side member includes an inner surface with a plurality of necked down regions and the second side member includes an inner surface with a plurality of necked down regions.

It is also a further object of the present invention to provide a device wherein a constraining band is fitted about the flex member.

It is yet a further object of the present invention to provide a device wherein the actuation mechanism includes a flexing finger which one may hold and move to cause articulation of the articulating assembly.

It is also an object of the present invention to provide a device wherein the flexing finger includes a constant stress beam having a tapered down cross section as it extends from a second end of the handle to a first end of the handle so that the flexing finger bends down in a smooth arc.

It is another object of the present invention to provide a device wherein the actuation mechanism includes a cable having a first end and a second end, the first end of the cable being coupled to the flexing finger and the second end being coupled adjacent the articulation assembly such that the cable moves to cover the increased arc length over which it is stretched as the flexing finger is bent.

It is a further object of the present invention to provide a device including first and second pulleys about which the cable is wrapped for amplifying the displacement of the cable.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and for teaching one skilled in the art how to make and/or use the invention.

Figure 1:
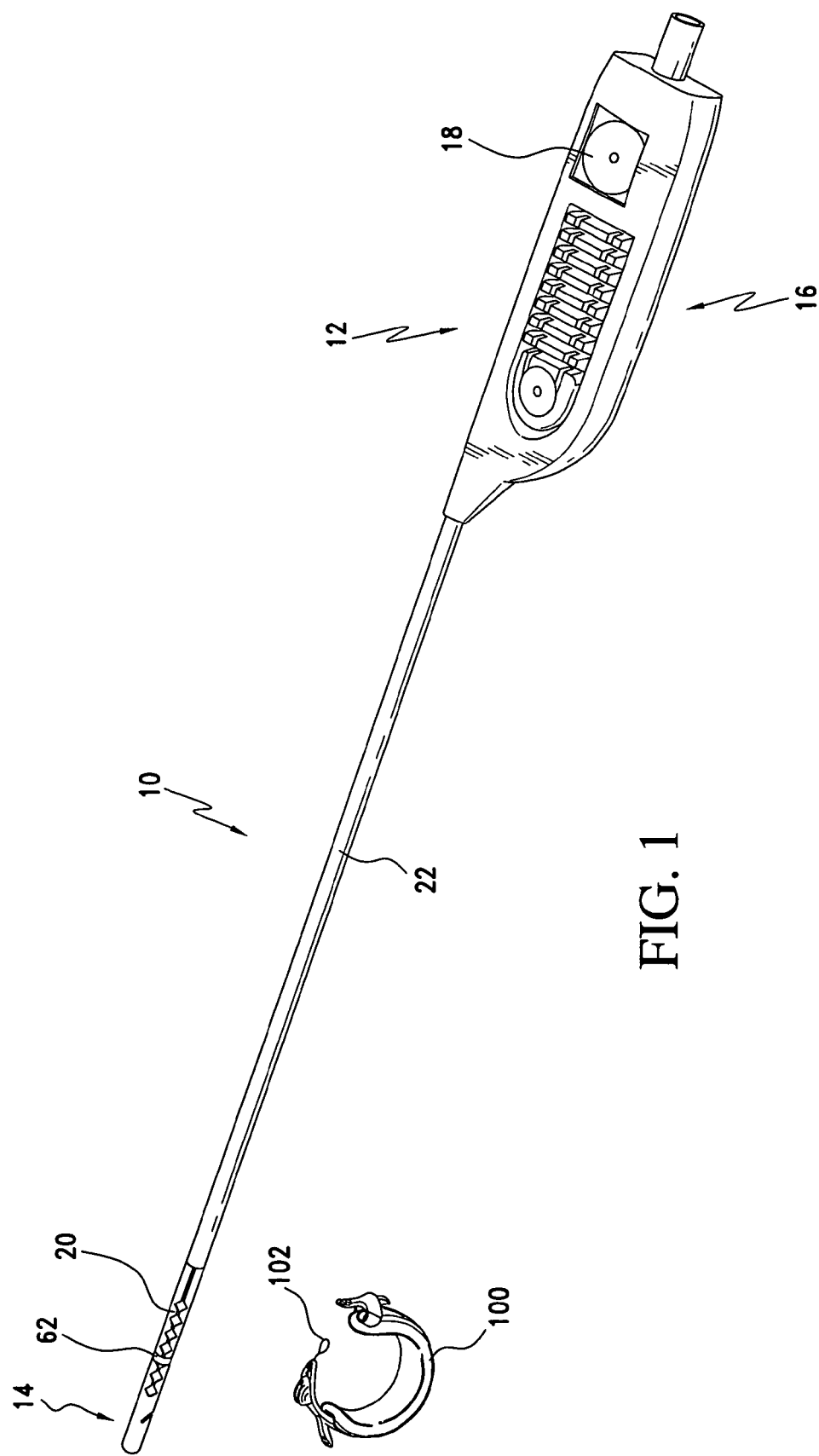
FIG. 1 is a perspective view of the present single handed articulating blunt dissector/gastric band application device.
Figure 2:
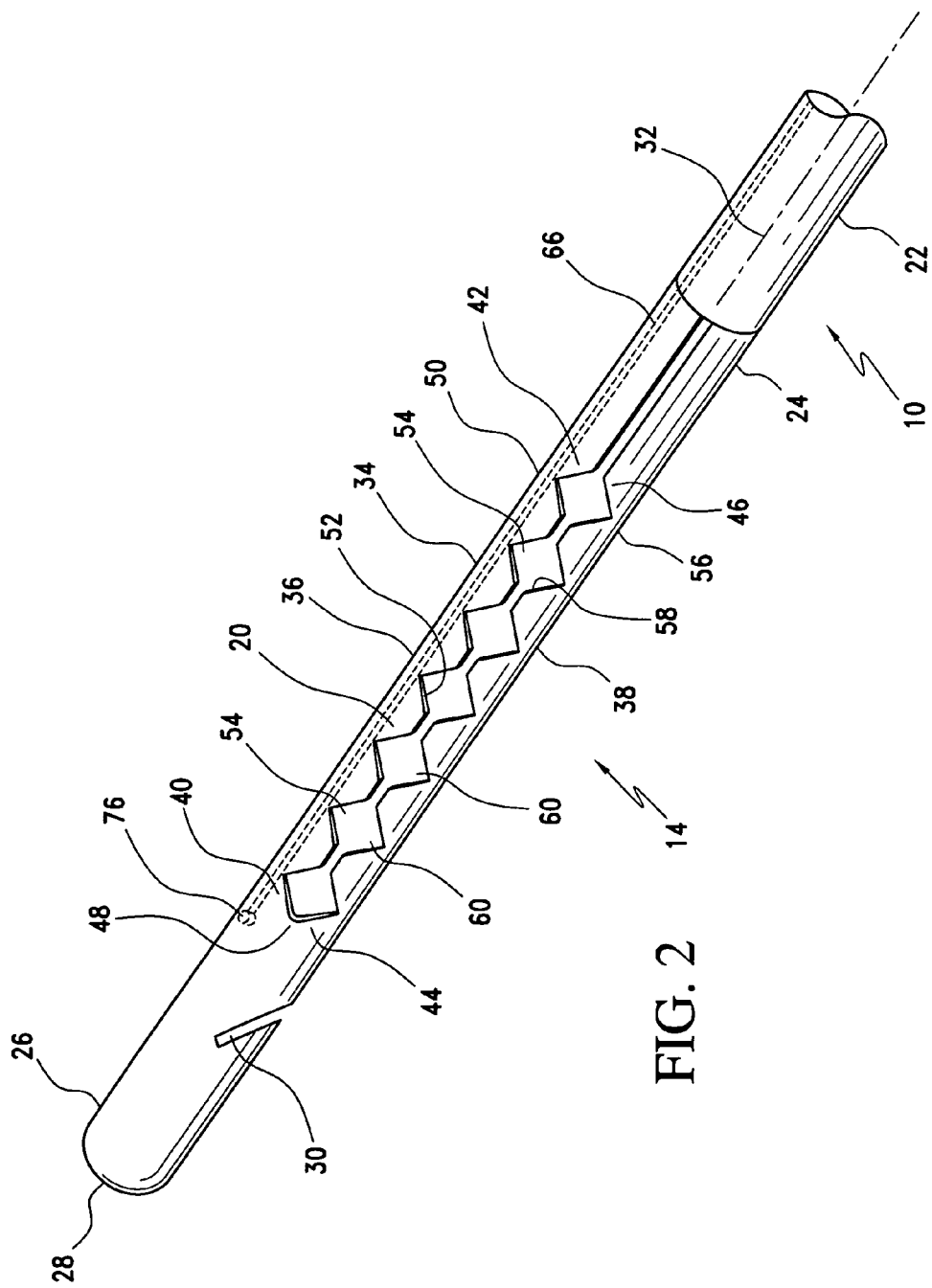
FIG. 2 is a detailed view of the second end of the application device shown with reference to FIG. 1 wherein the constraining band has been removed.
Figure 3:
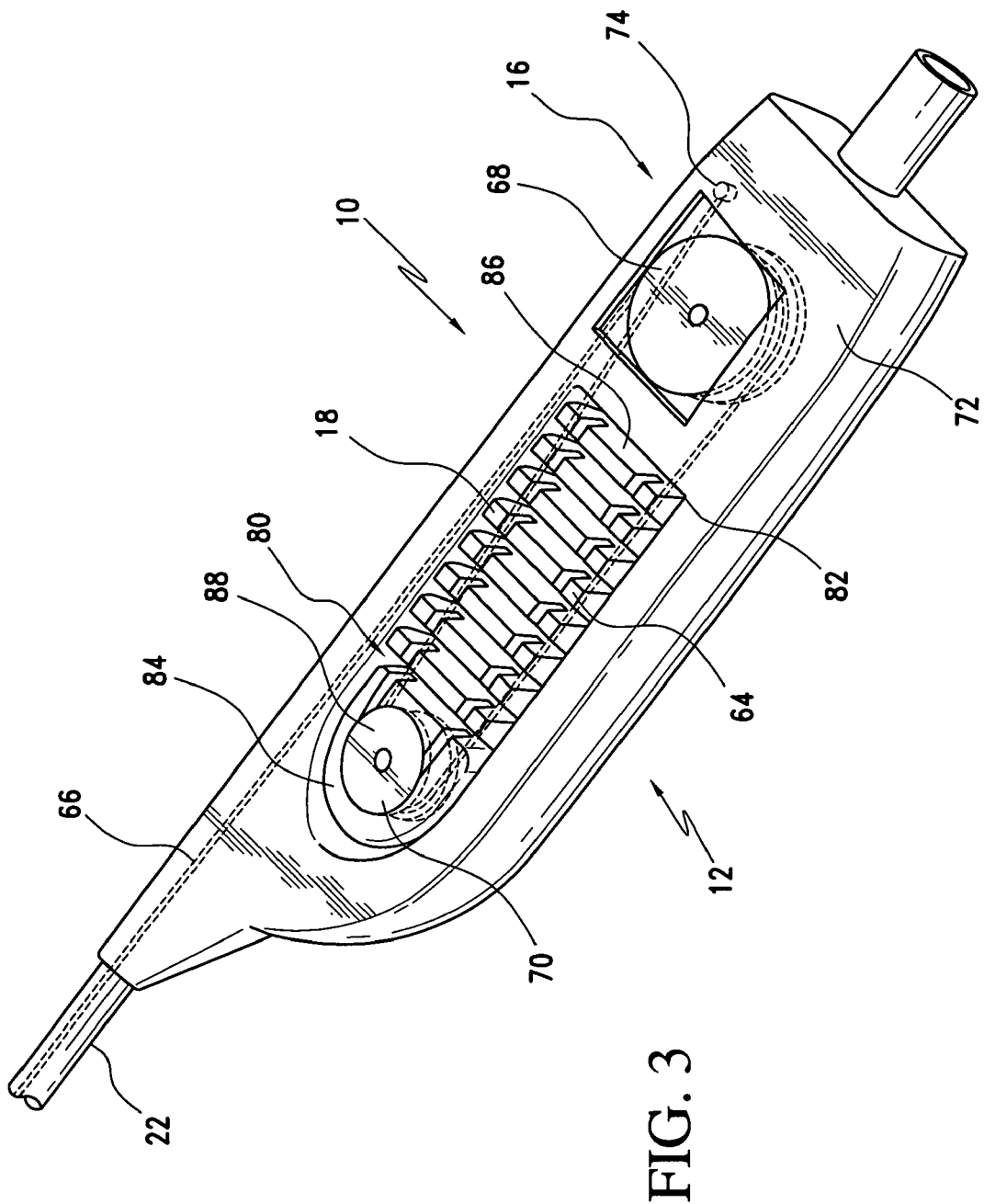
FIG. 3 is a detailed view of the first end of the application device shown with reference to FIG. 1.

Referring to FIGS. 1, 2 and 3, a single handed articulating blunt dissector/gastric band application device 10 is disclosed. The device 10 includes a first end 12 and a second end 14. The first end 12 is generally composed of the handle 16 and actuation mechanism 18 which are described below in greater detail. The second end 14 is composed of an articulating assembly 20 adapted for dissecting tissue, as well as engaging and manipulating a gastric band 100 during delivery thereof. Between the first and the second ends 12, 14 of the present device 10 is a support shaft 22 that connects the handle 16 at the first end 12 of the device 10 to the articulating assembly 20 at the second end 14 of the device 10. As those skilled in the art will appreciate, the present device 10 may be manufactured from a variety of biocompatible materials adapted for the specific purposes of the present invention.

As will be appreciated based upon the following disclosure, the second end 14 of the present device 10 includes a proximal end 24 and a distal end 26. The distal end 26 includes a blunt distal tip 28 shaped and dimensioned for dissecting tissue without unduly causing trauma to the tissue. Also at the distal end 26 of the second end 14 of the present device 10, and adjacent the distal tip 28, the second end 14 is provided with a suture grasping notch 30 for engaging and pulling the gastric band 100 through the retrogastric esophageal window. Referring to commonly owned U.S. Pat. No. 5,522,788 entitled "Finger-like laparoscopic blunt dissector device", which is incorporated herein by reference, gastric bands 100 are commonly provided with a suture loop 102 extending therefrom. The suture loop 102 provides a contact member allowing one to grasp the end of the gastric band 100 and draw it about the stomach for application thereof.

With this in mind, the second end 14 of the present application device 10 is provided with a notch 30 shaped and dimensioned for receiving the suture loop 102 in a manner allowing one to readily manipulate the gastric band 100 as it is applied about the stomach. In accordance with a preferred embodiment, the notch 30 is obliquely oriented relative to the longitudinal axis 32 of the present device 10 (that is, when it is in its straight configuration). More particularly, the notch 30 is oriented at a 45 degrees angle relative to the longitudinal axis 32 of the device 10 with the angular orientation directed toward the first end 12 of the device 10. As mentioned above, an articulating assembly 20 is positioned at the second end 14 of the device 10. The articulating assembly 20 is, however, proximally oriented relative to the notch 30 described above such that the articulating assembly 20 can be used to reorient the notch 30 for use thereof in wrapping a gastric band 100 about an individual's stomach. In general, the articulating assembly 20 is positioned between the proximal end 24 and the distal end 26 of the second end 14 of the present device 10. The articulating assembly 20 includes a flex member 34. The flex member 34 is composed of a single piece of flexible material, which is capable of bending as one side thereof is moved relative to the other side. In accordance with a preferred embodiment, the flexible material is nylon, although polyethylene and polypropylene are also good materials for use in the construction of the flexible material. Although specific materials are disclosed herein, other flexible materials could certainly be used without departing from the spirit of the present invention. More particularly, the flex member 34 includes a first side member 36 and a second side member 38. The first side member 36 and the second side member 38 are substantially parallel and are spaced from each other as they extend along the second end 14 of the present device 10. The first and second side members 36, 38 are relatively moveable to create the flex characteristics discussed below in greater detail.

The first side member 36 of the flex member 34 includes a first end 40 and a second end 42, while the second side member 38 of the flex member 34 includes a first end 44 a second end 46. The first ends 40, 44 of the respectively first and second side members 36, 38 of the flex member 34 are coupled to define the distal end 48 of the flex member 34, and ultimately extend into the distal end 26 of the second end 14 of the present device 10, which includes the previously discussed suture loop grasping notch 30 as discussed above.

The first side member 36 includes a substantially smooth outer surface 50. The inner surface 52 of the first side member 36 includes a plurality of necked down regions 54. The necked down regions 54 reduce the strength of the first side member 36 at predetermined locations therealong and facilitate bending by minimizing the articulation force required for movement thereof. Similarly, the second side member 38 includes a substantially smooth outer surface 56. The inner surface 58 of the second side member 38 includes a plurality of necked down regions 60. The necked down regions 60 reduce the strength of the second side member 38 at predetermined locations therealong and facilitate bending by minimizing the articulation force required for movement thereof. While the necked down regions 54, 60 of the first and second side members 36, 38 allow for controlled flexing of the flex member 34, the smooth outer surfaces 50, 56 allow for movement of the present device 10 through body cavities and tissue without causing undue trauma to the adjacent tissue.

In order to prevent the first and second side members 36, 38 from bending away from each other as loads are applied thereto in accordance with the present invention, a constraining band 62 is fitted about the flex member 34. The constraining band 62 flexes with the flex member 34 and moves therewith for preventing the first and second side members 36, 38 of the flex member 34 from separating. Although a constraining band 62 is disclosed in accordance with a preferred embodiment of the present invention, other constraining members, for example, an extension spring may be utilized without departing from the spirit of the present invention. The utilization of a constraining band 62 (or other constraining structure) is critical in allowing the flex member 34 to apply force in the direction in which it is flexed as well as in the opposite direction, without the first and second side members 36, 38 bowing outwardly upon the application of tension causing flexing of the present articulating assembly 20. By utilizing the constraining band 62, the flex member 34 is symmetrical and may flex in either direction, providing greater than 180° of articulation.

As mentioned above, the first end 12 of the device 10 is provided with the actuation mechanism 18 used in controlling flexing of the flex member 34. The actuation mechanism 18 includes a flexing finger 64 integrally formed with the handle 16. The flexing finger 64 is generally a readily flexible, elongated member which one may hold and move to cause articulation of the flex member 34 described above.

More particularly, the handle 16 is formed with a central opening 80 in which the flexing finger 64 is positioned. The central opening 80 includes a first end 82 and a second end 84 with the first end 86 of the flexing finger 64 being coupled to the handle 16 at the first end 82 of the central opening 80. The remainder of the flexing finger 64 is spaced from the handle 16. As such, the flexing finger 64 may bend about the first end 86 thereof, and within the central opening 80, as pressure is applied along the second end 88 of the flexing finger 64.

In accordance with a preferred embodiment, the flexing finger 64 is composed of nylon, although polyethylene and polypropylene are also good materials for use in the construction of the flexible material. Although specific materials are disclosed herein, other flexible materials could certainly be used without departing from the spirit of the present invention. As will be better appreciated based upon the following disclosure, the flex finger 64 uses a constant stress beam (tapered down cross section) so that flexing finger 64 bends down in a smooth arc along the length of the flexing finger 64 and stress is not concentrated at either the first end 86 or the second end 88 of the flexing finger 64.

A pull cable 66 is slideably coupled to the flexing finger 64 such that the cable 66 moves to cover the increased arc length over which it is stretched as the flexing finger 64 is bent. In addition to the cable 66, and in accordance with a preferred embodiment, pulleys 68, 70 are used to amplify the displacement of the cable articulating the flex member 34. The pulleys, for example, a first, or palm, pulley 68, which is positioned at the first end 72 of the handle 16 adjacent the first end 86 of the flex finger 64, and a second, or tip pulley 70, which is positioned at the second end 88 of the flex finger 64, may be static or free spinning. The pull cable 66 winds around the palm pulley 68 and extends to the first end 72 of the handle 16 where it is anchored. In this way, motion of the cable 66 translates into motion of the elements of the flexing finger 64, thereby articulating the flex member 34.

More particular, and in accordance with a preferred embedment, the cable 66 includes a first end 74 and a second end 76. The first end 74 is fixedly secured to the first end 72 of the handle and the second end 76 is fixedly secured to the second end 14 of the device 10 at a position beyond the flex member 34. The cable 66 is of a length such that it is slightly taut when the device 10 is straight and is tensioned when the flexing finger 64 is bent in a predetermined direction (as those skilled in the art will appreciate, and in accordance with a preferred embodiment, the cable 66 is loosened when the flexing finger 64 is bent in the other direction).

The flexing finger 64 and fixing point of the first end 74 of the cable 66 allow one to readily alter the effective length between the fixing point of the cable 66 at the second end 14 of the device 10 and the fixing point of the cable 66 at the first end 12 of the device 10. In particular, because the cable 66 is oriented over an outer surface of the flexing finger 64, when one bends the flexing finger 64 into a concave orientation when viewed from the side along which the cable 66 extends, the effective distance between the fixing point of the cable 66 at the second end 14 of the present device 10 and the fixing point of the cable 66 at the first end 12 of the device 10 increases, creating increased tension along the cable 66 and causing the flex member 34 to flex in the direction of the applied tension. Conversely, when one bends the flexing finger 64 into a convex orientation when viewed from the side along which the cable 66 extends, the effective distance between the fixing point of the cable 66 at the second end 14 of the present device 10 and the fixing point of the cable 66 at the first end 12 of the device 10 decreases, creating slack along the cable 66 and allowing it to remain in its relaxed configuration, which, in accordance with a preferred embodiment of the present invention, is straight.

Bending of the flex member 34, and the creation of tension, is further enhanced by the provision of a pulley system along the length of cable 66. In particular, first and second pulleys 68, 70 are respectively placed at the first end 72 of the handle 16 adjacent the first end 86 of the flexing finger 64 and the second end 88 of the flexing finger 64. The cable 66 is looped through the first and second pulleys 68, 70 adjacent the first end 74 thereof. In accordance with a preferred embodiment, and beginning at the first end 74 of the cable 66, the cable 66 extends up along the flexing finger 64 and is wrapped about the second pulley 70. The cable 66 continues back toward the first end 72 of the handle 16 and wraps about the first pulley 68. The cable 66 then extends up along the device 10 where the second end 76 of the cable 66 is secured at the second end 14 of the present device 10 at a position distal to the flex member 34 thereof.

In accordance with an alternate embodiment, the palm pulley may be a pinion such that rotary motion of the palm pulley moves a rack longitudinally along the shaft. This would create a push-pull configuration capable of both articulating and straightening the tip.

Through implementation of the present device 10, one may control the movement of the flex member 34 by simply flexing the flexing finger 64 in a manner similar to the flexation he/she wishes to create at the second end 14 of the present device 10. In fact, the present device 10 may be calibrated such that the flexing of the flexing finger 64 substantially corresponds to the flexing at the flex member 34 at the second end 14 of the device 10.

As mentioned above, the device is particularly adapted for delivery, manipulation and application of gastric bands about the stomach of an individual. With this in mind, a gastric band 100 is inserted behind the stomach and the first and second ends thereof are manipulated with the present device until the band is securely positioned about the stomach. The present device is adapted for use with a variety of gastric bands, for example, those disclosed in commonly owned and copending U.S. patent application Ser. No. 11/364,362, entitled "Gastric Band", which is incorporated herein by reference. It will become readily apparent to those skilled in the art that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. Patent Application Publication No. 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. Patent Application Publication No. 2003/0114729, which is hereby incorporated herein by reference.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. A single handed articulating blunt dissector/gastric band application device, comprising:
   a support shaft connecting a handle at a first end of the device to an articulating assembly at a second end of the device;
   the handle includes an actuation mechanism linked to the articulating assembly for controlling movement thereof wherein the actuation mechanism includes a flexing finger which one may hold and move to cause articulation of the articulating assembly, and the handle is formed with a central opening in which the flexing finger is positioned, the central opening including a first end and a second end with a first end of the flexing finger being coupled to the handle at the first end of the central opening and a remainder of the flexing finger is spaced from the handle allowing the flexing finger to bend about the first end thereof as pressure is applied along the second end of the flexing finger resulting in controlled movement of the articulating assembly;
   the second end includes a proximal end and a distal end, wherein the distal end includes a blunt distal tip, and the second end also includes a suture grasping notch shaped and dimensioned for engaging and pulling a gastric band, the suture grasping notch being formed in the blunt distal tip wherein the suture grasping notch is obliquely oriented relative to a longitudinal axis of the application device when the application device is in a straight configuration.

2. The device according to claim 1, wherein the suture grasping notch is oriented at 45 degree angle relative to the longitudinal axis of the device.

3. The device according to claim 1, wherein the articulating assembly is proximally oriented relative to the suture grasping notch.

4. The device according to claim 1, wherein the articulating assembly includes a flex member composed of a first side member and a second side member.

5. The device according to claim 4, wherein the first side member and the second side member are substantially parallel and are spaced from each other as they extend along the second end of the device.

6. The device according to claim 4, wherein the first side member includes an inner surface with a plurality of necked down regions and the second side member includes an inner surface with a plurality of necked down regions.

7. The device according to claim 4, wherein a constraining band is fitted about the flex member.

8. The device according to claim 1, wherein the flexing finger includes a constant stress beam having a tapered down cross section as it extends from the second end of the handle to the first end of the handle so that the flexing finger bends down in a smooth arc.

9. The device according to claim 1, wherein the actuation mechanism includes a cable having a first end and a second end, the first end of the cable being coupled to the flexing finger and the second end being coupled adjacent the articulation assembly such that the cable moves to cover the increased arc length over which it is stretched as the flexing finger is bent.

10. The device according to claim 9, further including first and second pulleys about which the cable is wrapped for amplifying the displacement of the cable.

* * * * *